United States Patent [19]

Kowalski

[11] 4,034,223
[45] July 5, 1977

[54] DEVICE FOR MEASURING RADIATION ABSORPTION

[75] Inventor: Gunter Kowalski, Hamburg, Germany

[73] Assignee: U.S. Philips Corporation, New York, N.Y.

[22] Filed: Jan. 28, 1976

[21] Appl. No.: 653,111

[30] Foreign Application Priority Data

Jan. 30, 1975 Germany ............................ 2503789

[52] U.S. Cl. ............................... 250/369; 250/360; 250/393; 250/445 T
[51] Int. Cl.² ............................................ G01T 1/20
[58] Field of Search ....... 250/360, 359, 312, 445 T, 250/460, 393, 394, 369

[56] References Cited

UNITED STATES PATENTS 3,099,746   7/1963   Walter .............................. 250/360
3,106,640  10/1963   Oldendorf ......................... 250/360
3,881,110   4/1975   Hounsfield ........................ 250/360

Primary Examiner—Harold A. Dixon
Attorney, Agent, or Firm—Frank R. Trifari

[57] ABSTRACT

In computerized tomographic scanning systems it is desirable to reduce the scanning time required. Therefore, it is desirable that the radiation source/radiation detector system not be stopped and subsequently accelerated again for each absorption measurement. The present system continuously rotates and the source is continuously turned on, the output signal of each radiation detector being applied via a low-pass filter to a sample-and-hold circuit having a sampling frequency which is about twice as high as the limit frequency of the low-pass filter. Better accuracy is obtained than with known scanners having discontinuous movement or a flashing radiation source.

4 Claims, 2 Drawing Figures

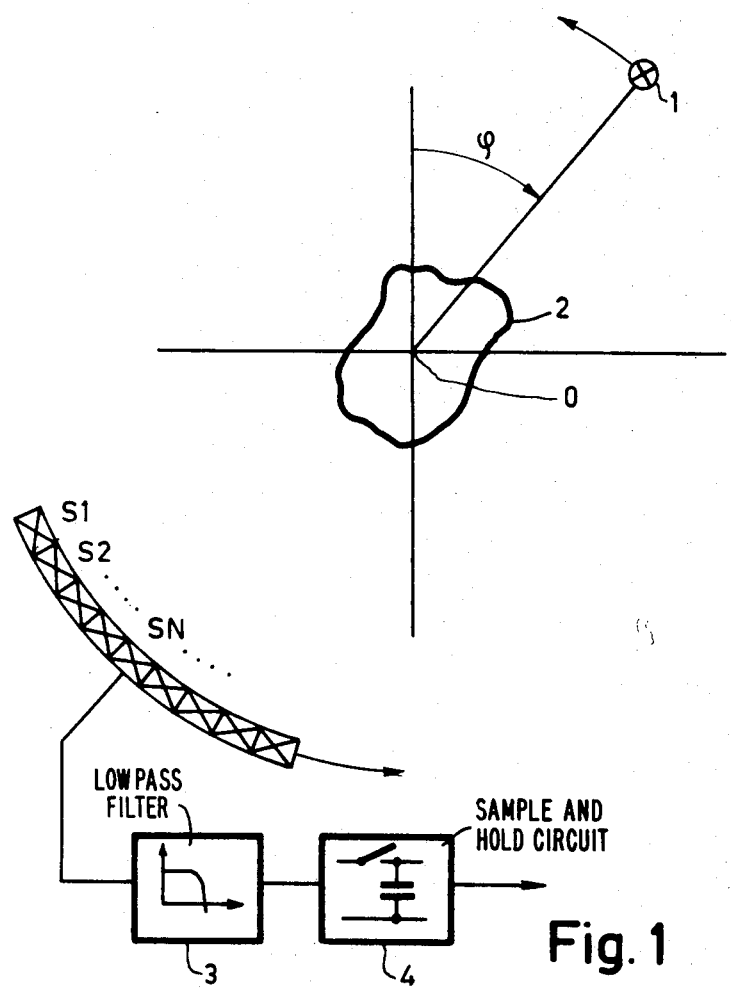
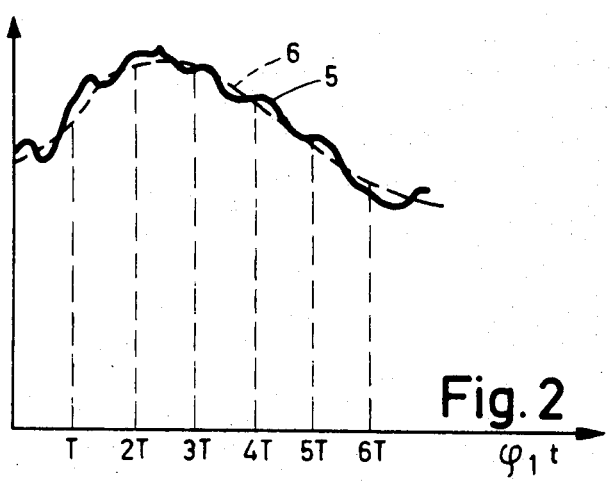
Fig. 1
Fig. 2

DEVICE FOR MEASURING RADIATION ABSORPTION

The invention relates to a device for measuring the absorption of radiation in a plane of a body, comprising a radiation source and a plurality of radiation detectors which are arranged respectively in the same plane on opposite sides of the body, the radiation source/radiation detector system being continuously movable, preferably rotatable, with respect to the body, the absorption of the body being measured in different orientations of the system.

A device of this kind is known, for example, from the previous Patent Application P 24 42 809 in the name of Applicant. On the basis of absorption values measured by means of this device in different orientations of the radiation source/radiation detector system, the absorption at each point in a plane to be examined is calculated by means of a computer. The radiation source and the radiation detectors are moved along a circular trajectory about the object. The movement can either by continuous, in which case the radiation source is flashed, i.e. it is briefly switched on so that the amount of displacement in the switched-on condition is negligibly small, or the radiation source/radiation detector system can be step-wise rotated through a given angle, the radiation source always being switched on only in the rest condition between relational steps.

When the radiation source is an X-ray source, the operational flashing is very difficult to realize in practice if at all. On the other hand, the step-wise movement of the radiation source and the radiation detectors and the stopping of the radiation source during the switching on necessitate the periodic acceleration and braking of a particularly large mass. Therefore, a complete measurement during which the radiation source and the radiation detectors pass through an angle of 180° or 360° on the circular trajectory can only be performed slowly. This is a drawback if the radiation absorption or the density of the tissue to be examined is in a plane of the body of a patient who cannot be kept still for an arbitrarily long period. Moreover, both methods of measurement have in common that a symmetrical error occurs when the radiation field of view covered by a single radiation detector is small in comparison with the trajectary or the angle through which the radiation source/radiation detector system is displaced between two measurements.

The invention has for its object to provide a simple and accurate device of the kind set forth. This object is achieved in that the radiation source is continuously activated during the continuous movement, the output signal of each radiation detector being applied, via a low-pass filter, to a sampling device which periodically samples the output signal.

The invention will be described in detail hereinafter with reference to the drawing.

FIG. 1 is a substantially simplified diagrammatic representation of the device of the invention, and FIG. 2 shows the variation in time of the output signal of a radiation detector.

FIG. 1 shows an X-ray source 1 and a number of radiation detectors S1, S2, SN etc. which are adjacently arranged in an arc with respect to the object to be examined and opposite the X-ray source. Between the radiation source and the radiation detectors there is situated the body 2 which attenuates the X-rays emitted by the radiation source 1 in dependence on the thickness and the density so that the output signal of different radiation detectors is dependent on the thickness and the density of the portion of the body 2 present between the radiation source 1 and the relevant radiation detector. The radiation source 1 and the radiation detectors are rotatable together, by means of a suitable device (not shown), at a constant angular speed about an axis O perpendicular to the plane to be examined.

Each radiation detector has associated with it a low-pass filter 3 whose output signal is applied to the input of a sample-and-hold circuit which periodically samples the output signal of the low-pass filter 3 and stores this signal until the next sampling instant. For simplicity's sake, the drawing shows only the low-pass filter associated with the radiation detector SN and also the sample-and-hold circuit connected to this filter.

The uninterrupted curve 5 in FIG. 2 denotes the variation of the output signal of the radiation detector in dependence on the angle $\theta$ of the radiation source/radiation detector system or — because a linear relationship exists between the angle of rotation and the time — in dependence on the time. In the device described in the said previous Patent Application, only the value of the output signal occurring at periodic instants (T, 2T, 3T etc.) is processed. Because, as is shown, the output signal — determined by the fine structures in the object — changes comparatively quickly between two sampling instants, and hence contains components of a frequency substantially higher than the sampling frequency, systematic errors occur, because in accordance with the sampling theorem error-free sampling of a signal is possible only if it does not contain frequency components larger than half the sampling frequency. The output signal of a radiation detector (in the case of a continuously switched on radiation source), however, can contain such frequency components and, consequently, in the known device it may occur that at the sampling instant the signal from the detector is falsified by a peak or dip of short duration in comparison with the sampling period.

This error is avoided in the device embodying the invention in that the output signal of each radiation detector is conducted via a low-pass filter 3 whose limit frequency corresponds to approximately half the sampling frequency (½T), with the result that all higher frequency components which could cause errors during the subsequent evaluation are eliminated. The output signal of the low-pass filter is denoted by the broken curve 6 in FIG. 2. This output signal is sampled and stored by the subsequent sample-and-hold circuit 4 at periodic instants (T, 2T, 3T etc.) or after the passing through of each time a given angle (for example, 3°, 6°, 9° etc.). The output signal of the sample-and-hold circuit 4 is further processed in known manner (see German Offenlegungsschrift 1,941,433). The required calculation of the logarithm can be effected either before or after the low-pass filter.

The device embodying the invention is comparatively simple, because the radiation source need not be "flashed", but is continuously switched on, and a complete measurement can be performed comparatively quickly because the radiation source/radiation detector system need not be stopped to obtain a constant sampling value, but may continuously rotate at a constant speed.

If, instead of a radiation detector supplying an output signal having an amplitude which is dependent on the intensity of the radiation, use is made of a radiation detector which supplies a number of pulses in dependence on the radiation intensity, the low-pass filtering action can be approximated by integration or summation of the pulses over a sampling period.

If the intensity of the radiation source is modulated, for example, by a correspondingly modulated direct current power supply, or mechanically by means of a moving grid (see German Offenlegungsschrift 2,452,166), the output signal of each radiation detector contains, besides a direct current component, a carrier frequency about which a spectrum occurs in accordance with the modulation by the density of the object. The low-pass filtering action could then be realized either by demodulation of the output signal, followed by application to a low-pass filter whose output is connected to the sampling device, or by application of the output signal of each radiation detector to the sampling device via a band-pass filter and a demodulator; in the latter case, the mid-frequency of the band-pass filter should correspond to the carrier frequency and the bandwidth should correspond to the sampling frequency.

What is claimed is:

1. In apparatus for measuring the absorption of radiation in a plane of a body of the type wherein a radiation source and a plurality of detectors are arranged in the same plane on opposite sides of the body and uniformly moved relative to the body at a constant speed, the improvement comprising, with respect to each detector:
   means for removing from the output signal of the detector all absorption signal frequency components which are above a limit frequency; and
   means for periodically sampling the frequency limited absorption signal of the detector, the limit frequency being approximately half of the sampling frequency to thereby avoid sampling errors.

2. Apparatus as defined in claim 1 wherein the uniform movement of the radiation source and detectors relative to the body is rotary movement thereof at a constant speed about an axis perpendicular to the plane.

3. Apparatus as defined in claim 2 wherein the output signal of the detector is an analog signal and said means for removing frequency components comprises a low-pass filter.

4. Apparatus as defined in claim 3 wherein said means for periodically sampling comprises a sample-and-hold circuit.

* * * * *